(12) United States Patent
Dicks

(10) Patent No.: US 6,338,220 B1
(45) Date of Patent: Jan. 15, 2002

(54) ERADICATION OF MOSQUITOES

(75) Inventor: Graeme Kingston Dicks, c/o Fairiedene Thatchers, 1 Dicks Building, 94 Old Main Road, Pinetown, 3610 (ZA)

(73) Assignee: Graeme Kingston Dicks, Pinetown (ZA)

( * ) Notice: Subject to any disclaimer, the term of this patent is extended or adjusted under 35 U.S.C. 154(b) by 0 days.

(21) Appl. No.: 09/265,838

(22) Filed: Mar. 10, 1999

(51) Int. Cl.[7] ................................................. A01M 1/20
(52) U.S. Cl. ...................................................... 43/132.1
(58) Field of Search ........................... 43/132.1; 119/69.5

(56) References Cited

U.S. PATENT DOCUMENTS 2,165,753 A * 7/1939 Hobbs
3,696,786 A * 10/1972 Garwood .................... 119/69.5
3,995,591 A * 12/1976 Garwood .................... 119/69.5
4,630,569 A * 12/1986 Dieleman ................... 119/69.5
5,692,454 A * 12/1997 Testa ........................... 119/69.5

* cited by examiner

*Primary Examiner*—Thomas Price
(74) *Attorney, Agent, or Firm*—Burns Doane Swecker & Mathis LLP

(57) ABSTRACT

The invention relates to a method of eradicating mosquitoes, which includes the steps of inducing female mosquitoes to lay their eggs in the vicinity of water contained in an open-topped container provided for the purpose, causing the larvae in which form the eggs hatch to live in the water. The water is then emptied from the container together with the larvae, before the larvae changes into the adult form of mosquitoes, resulting in the larvae dying because of the larvae not being exposed to water. The invention relates also to apparatus provided for carrying out the above method repetitively over extended time periods.

9 Claims, 3 Drawing Sheets

ERADICATION OF MOSQUITOES

This invention relates to the eradication of mosquitoes.

More particularly, the invention relates to a method of and apparatus for eradicating mosquitoes, particularly by breaking the breeding cycle of mosquitoes and thereby preventing breeding of mosquitoes.

The breeding cycle of mosquitoes commences with adult female mosquitoes laying eggs, particularly in the near vicinity of a stagnant or relatively still pool of water. After a period of time the eggs will hatch, providing mosquito larvae that require to live in water in order to survive. The mosquito larvae therefore will immerse themselves in the water near which the eggs were laid and over a period of three or four days will change into the adult form of mosquitoes.

Accordingly, it is an object of this invention to eradicate mosquitoes by breaking the above described breeding cycle of mosquitoes.

According to the invention there is provided a method of eradicating mosquitoes, which comprises providing an open-topped container for holding water;

introducing water into the container in order to attract female mosquitoes to lay eggs in the vicinity of the water, which eggs will then hatch in the form of larvae that will live in the water; and emptying all of the water introduced into the container upon the expiry of a predetermined time period, which period is less than the life span of mosquito larvae within which the larvae changes into the adult form of mosquitoes.

The method may include, after emptying of all the water introduced into the container, repeating continuously the process of introducing water into the container and emptying water so introduced upon the expiry of the predetermined time period.

The method of the invention also may include determining the life span of the species of mosquito larvae existing in the area where the method is to be employed and providing for emptying of the container within time periods shorter than the determined life span of the mosquito larvae.

Still further, the method may include locating a mosquito attracting substance in the vicinity of the container for attracting female mosquitoes about to lay eggs to the container and thereby providing for the female mosquitoes to lay their eggs in the vicinity of the container.

Further according to the invention, the method includes providing with the container water feed means and a water discharge arrangement, whereby the introduction of water into the container and emptying of water from the container can be repeated continuously.

In accordance with the method of the invention, by introducing water into the container that is provided, female mosquitoes will be attracted to the water and induced to lay their eggs in the vicinity of the water. As mosquito larvae require water to survive, upon hatching of the larvae from the eggs, the larvae will immerse themselves in the water in the container. As such, when the water is emptied from the container on to the ground or wherever else the water is discharged, the larvae in the water will die soon afterwards, particularly when the water dissipates due to seepage into the ground, evaporation, or otherwise. Thereby, the method in accordance with the invention effectively interrupts the breeding cycle of mosquitoes, greatly reducing the mosquito population in the general area of the container and in effect providing for eradication of mosquitoes in the area.

A further aspect of the invention provides for apparatus for eradicating mosquitoes, which comprises an open-topped container for holding water;

water feed means for feeding water into the container; and a water discharge arrangement for causing water fed into the container to be discharged from the container at predetermined interval periods, each period being less than the life span of mosquito larvae that may develop in the water.

The water discharge arrangement of the apparatus may include a support structure which supports the container in an arrangement in which it is pivotally displaceable about a pivot axis between a first position wherein the container can hold water and a second position wherein the container is tilted with respect to its pivot axis and any water therein is discharged therefrom, the support structure defining an arrangement relative to the container in which sufficient uneven forces will act on the container relative to the pivot axis of the container to provide for tilting of the container from its first position to its second position when a critical predetermined volume of water has been fed into the container by the water feed means and reverse tilting will occur following emptying of all the water from the container.

The water feed means accordingly may be operable to feed water into the container from a pressurised water supply at a predetermined controlled flow rate which will provide for the said critical predetermined volume of water fed into the container being reached within a time period less than the life span of mosquito larvae that may develop in the water.

The apparatus further may include urging means for urging the container into its first position so that tilting of the container to its second position will occur against the force of the urging means.

According to a preferred embodiment of the apparatus of the invention, the container defines an elongate configuration, the container having a base wall, two side walls and two end walls with the side walls tapering towards one another from one end wall to the other end wall to define a wider end and a narrower end of the container, thereby providing for a greater proportion of the volume of water fed into the container to collect at the wider end of the container and causing the required uneven forces to act on the container to provide for tilting of the container from its first position to its second position when a critical predetermined volume of water has been fed into the container.

The apparatus still further may include mosquito attracting means for attracting female mosquitoes about to lay eggs to the container and thereby providing for the female mosquitoes to lay their eggs in the vicinity of the container, in use of the apparatus.

Further features of an apparatus for eradicating mosquitoes and a method of eradicating mosquitoes in accordance with the invention, are described hereinafter, by way of a non-limiting example of the invention, with reference to and as illustrated in the accompanying diagrammatic drawings. In the drawings.

Figure 1:
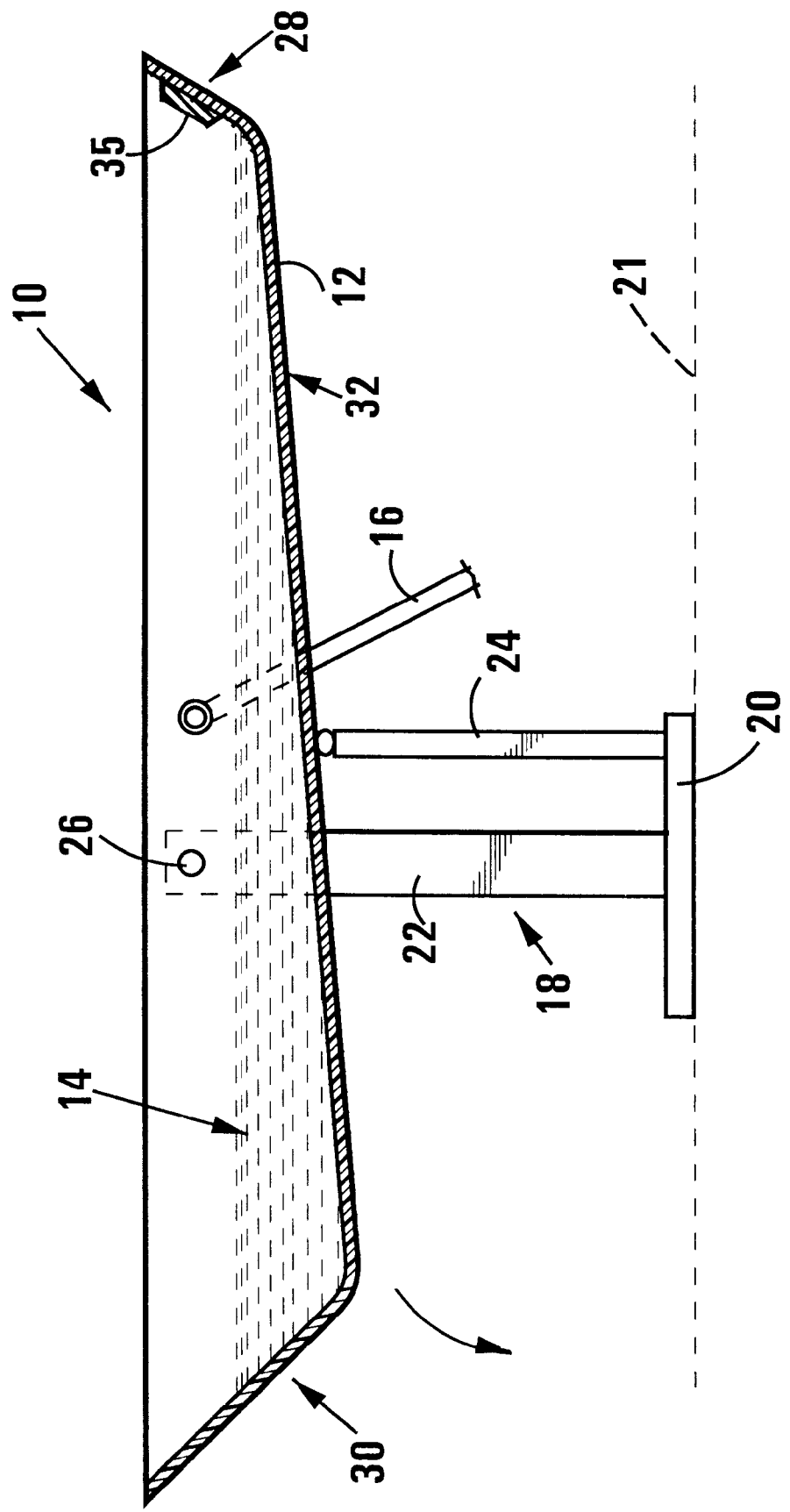
FIG. 1 shows a schematic side view of an apparatus for eradicating mosquitoes in accordance with the invention, with the container thereof being disposed in a first position.

An apparatus for eradicating mosquitoes in accordance with the invention, is designated generally by the reference numeral 10. The apparatus 10 comprises, broadly, an open-topped container 12 for holding water 14, water feed means for feeding water into the container and a water discharge arrangement for discharging water from the container 12 at predetermined times as described hereafter.

Figure 2:
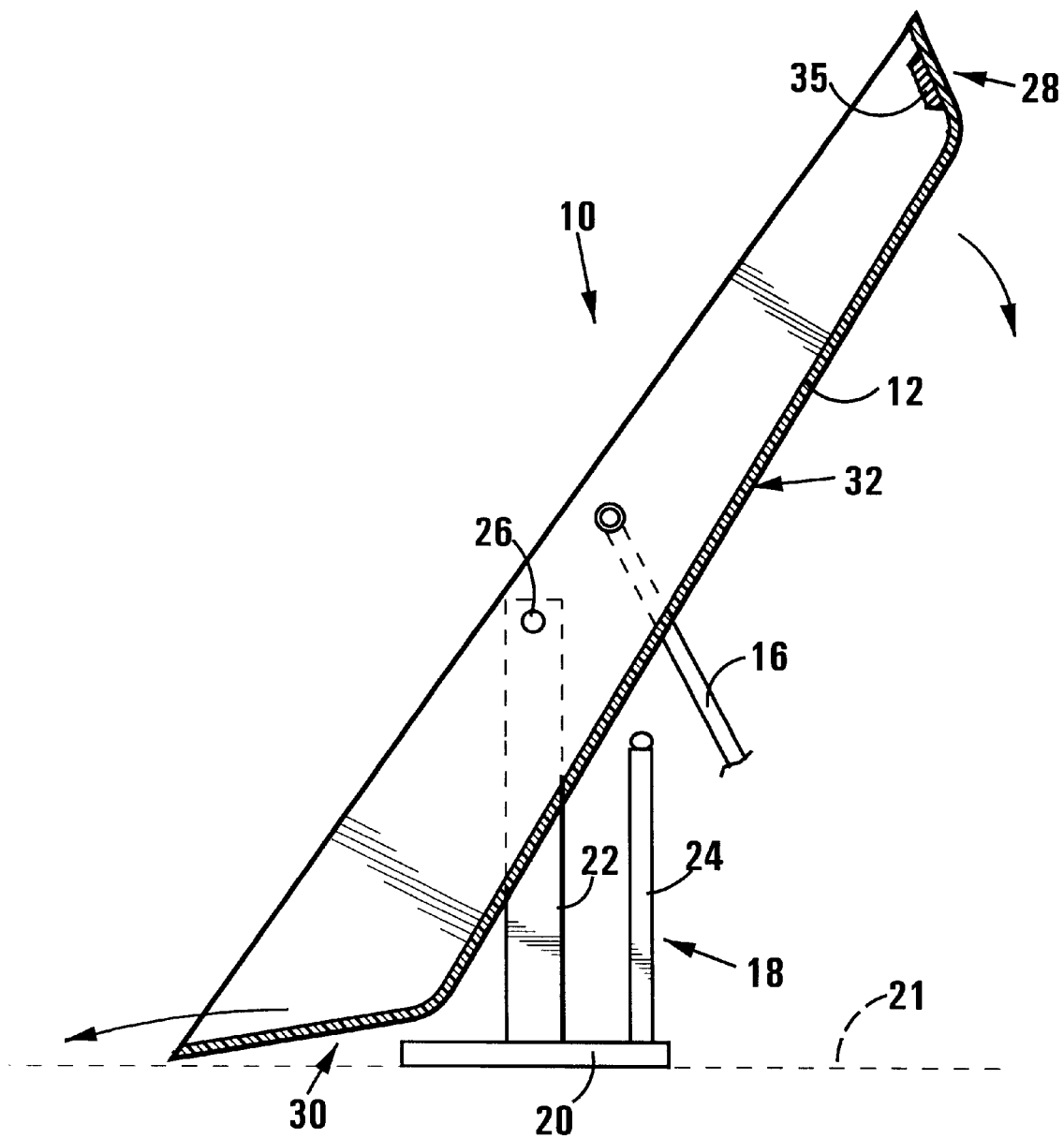
FIG. 2 shows a schematic side of the apparatus of FIG. 1, with the container being disposed in a second position.
Figure 3:
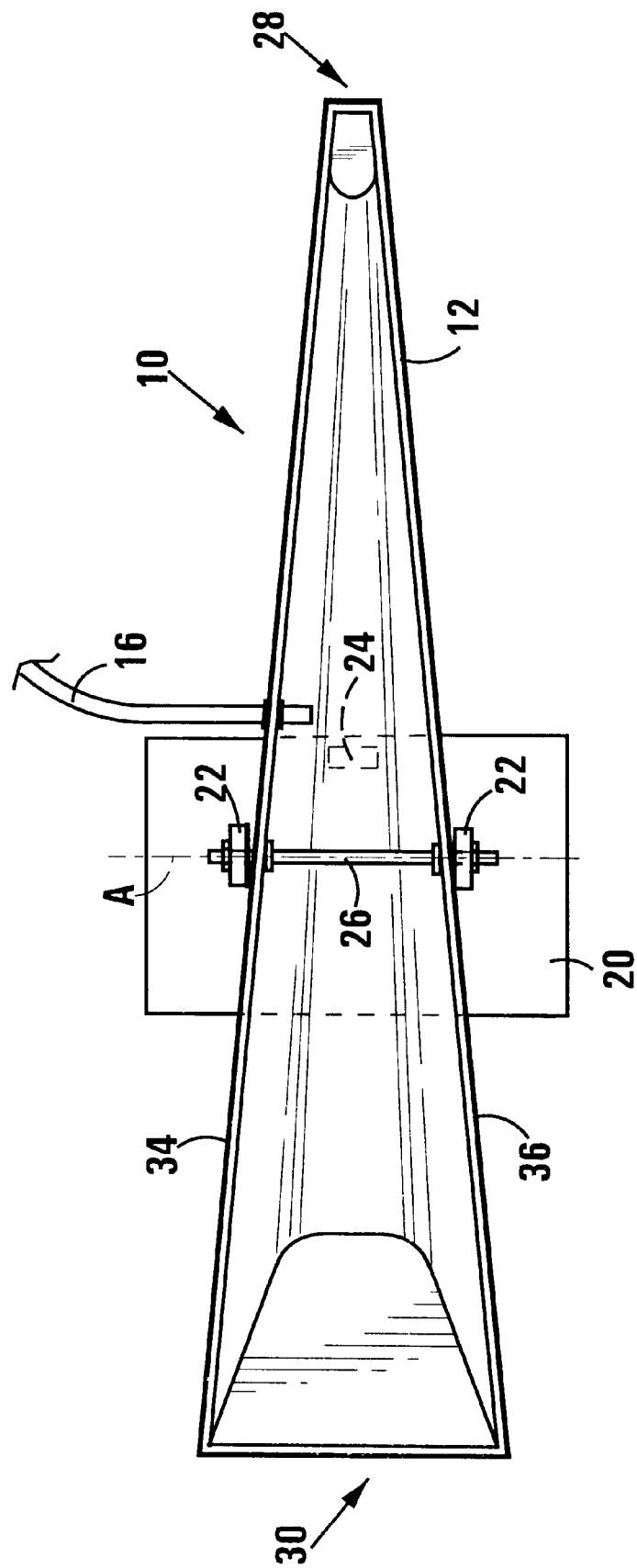
FIG. 3 shows a schematic top plan view of the apparatus of FIG. 1.

The water feed means is in the form of a pipe 16 of a predetermined diameter along which water from a water mains supply can flow at a predetermined flow rate, whereas the water discharge arrangement is in the form of a support structure 18 for supporting the container. The support structure 18 comprises a base 20 that can be positioned on a ground surface 21, two spaced opposed side support posts 22 and a base support post 24. The support structure 18 supports the container 12 in an arrangement wherein it is pivotally displaceable about a pivot axis A between a first position wherein the container can hold water (as is illustrated in FIG. 1 of the drawings) and a second position wherein the container is tilted with respect to its first position and any water therein is discharged therefrom (as is illustrated in FIG. 2 of the drawings). More particularly, the container 12 is pivotally supported on a pivot pin 26 that extends between the support posts 22.

The container 12 has an elongate configuration having two end walls 28 and 30, a base wall 32 and two side walls 34 and 36. The container 12 narrows from its end wall 30 to its opposite end wall 28, thereby permitting a greater volume of water to collect at the relatively wider end region of the container near its end wall 30. This causes an uneven mass distribution of water in the container which causes it to be displaced into its second position when a critical uneven mass distribution of water is achieved. The container 12 includes a mass-piece 35 that is located at the end wall 28.

In use, the container rests, via its base wall 32, on the base support post 24. Water from the pipe 16 enters the container via an opening in its side wall 34. The flow rate at which water enters the container 12 is controlled so as to provide for a critical volume of water to be fed into the container sufficient to cause it to be displaced into its second position upon the expiry of a predetermined period of time which is less than the life span of mosquito larvae that may develop in the water. As such, the mass-piece 35 acts as a counterweight which holds the container in its first position until a critical volume of water enters the container, sufficient to cause it to be displaced into its second position. As such, with the lifespan of mosquito larvae being in the region of three to four days, the Applicant envisages that the flow rate of water into the container will be adjusted so as to allow a critical volume of water to be achieved within two to three days.

After the water has been discharged from the container, the container is again returned to its first position under the action of the mass piece 34 and the process is repeated for as long as water is supplied to the container at said flow rate. When the water is discharged from the container, the larvae in the water will die soon afterwards when the water dissipates due to seepage into the ground, evaporation or otherwise.

The apparatus 10 includes a mosquito attracting substance that is applied to one or more surfaces of the support structure 18 for attracting mosquitoes to the apparatus.

The invention extends to two or more apparatus 10 that are supplied with water at said flow rate from a common water supply pipe which feeds water into the water pipes 16 of each apparatus 10. As such, the Applicant envisages that a number of apparatus 10 can be linked in series to cover a relatively large area such as, for example, a nature reserve.

The invention extends to a method of eradicating mosquitoes, which comprises, firstly, providing the container 12, secondly, introducing a predetermined amount of water into the container to attract female mosquitoes to lay eggs in the vicinity of the water which will hatch in the form of larvae that will live in the water, and, thirdly, emptying all of the water from the container upon the expiry of a predetermined period of time which is less than the lifespan of any mosquito larvae that may develop in the water.

The Applicant believes that the apparatus for eradicating mosquitoes, in accordance with the invention, provides a simple yet effective apparatus for eradicating large numbers of mosquito larvae which will result in a drastic reduction of mosquito numbers in the general area of the apparatus.

What is claimed is:

1. A method of eradicating mosquitoes, which comprises providing an open-topped container for holding water;
   introducing water into the container in order to attract female mosquitoes to lay eggs in the vicinity of the water, which eggs will then hatch in the form of larvae that will live in the water; and
   emptying all of the water introduced into the container upon the expiry of a predetermined time period, which time period is less than the life span of mosquito larvae within which the larvae changes into the adult form of mosquitoes.

2. A method as claimed in claim 1, which includes, after emptying of all the water introduced into the container, repeating continuously the process of introducing water into the container and emptying water so introduced upon the expiry of the predetermined time period.

3. A method as claimed in claim 1, which includes determining the life span of the species of mosquito larvae existing in the area where the method is to be employed and providing for emptying of the container within time periods shorter than the determined life span of the mosquito larvae.

4. A method as claimed in claim 1, which includes locating a mosquito attracting substance in the vicinity of the container for attracting female mosquitoes about to lay eggs to the container and thereby provide for the female mosquitoes to lay their eggs in the vicinity of the container.

5. A method as claimed in claim 1, which includes providing with the container water feed means and a water discharge arrangement, whereby the introduction of water into the container and emptying of water from the container can be repeated continuously.

6. Apparatus for eradicating mosquitoes, which comprises an open-topped container for holding water, the container defining an elongate configuration and having a base wall, two side walls and two end walls with the side walls tapering towards one another from one end of the container to the other end of the container to define a wider end and a narrower end of the container;
   water feed means for feeding water into the container at a controlled flow rate; and
   a water discharge arrangement for causing water, when fed into the container at a controlled flow rate, to be discharged therefrom at predetermined interval periods that are shorter than the life span of mosquito larvae that could develop in the water, the water discharge arrangement including a support structure which pivotally supports the container in an arrangement in which it is pivotally displaceable about a pivot axis between a first position, wherein the container can hold water therein, and a second position, wherein the container is tilted with respect to the first position and water held therein is discharged therefrom, the wider end and the narrower end of the container providing for a greater volume of water fed into the container to collect at a wider end of the container and causing an uneven force to act on the container relative to the pivot axis to provide for tilting of the container from its first position to its second position, when a predetermined critical volume of water is held in the container, while the container will return from its second position to its first position after water has been discharged therefrom.

7. An apparatus as claimed in claim 6, in which the water feed means is operable to feed water into the container from a pressurized water supply at a predetermined controlled flow rate which will provide for the said critical predetermined volume of water fed into the container being reached within a time period less than the life span of mosquito larvae that may develop in the water.

8. Apparatus is claimed in claim 6, which includes urging means for urging the container into its first position and in which tilting of the container to its second position will occur against the force of the urging means.

9. Apparatus as claimed in claim 6, which includes mosquito attracting means for attracting female mosquitoes about to lay eggs to the container and thereby providing for the female mosquitoes to lay their eggs in the vicinity of the container, in use of the apparatus.

* * * * *